United States Patent [19]

Hoffman et al.

[11] 4,287,987
[45] Sep. 8, 1981

[54] SUTURE HOLDER

[75] Inventors: Luther A. Hoffman, Sinking Spring; Friedrich W. Schmidt, Ephrata, both of Pa.

[73] Assignee: Sharpoint, Inc., Mohnton, Pa.

[21] Appl. No.: 59,677

[22] Filed: Jul. 23, 1979

[51] Int. Cl.³ .............................................. A61L 17/02
[52] U.S. Cl. .................................. 206/63.3; 206/227; 206/382; 43/57.5 R
[58] Field of Search ................... 206/63.3, 45.33, 388, 206/382, 383, 227; 43/57.5 R

[56] References Cited

U.S. PATENT DOCUMENTS

| | | | |
|---|---|---|---|
| 2,590,799 | 3/1952 | Solowey | 206/45.33 |
| 2,839,185 | 6/1958 | Isaacs | 206/45.33 |
| 4,183,431 | 1/1980 | Schmidt et al. | 206/63.3 |

*Primary Examiner*—William T. Dixson, Jr.
*Attorney, Agent, or Firm*—M. Richard Page

[57] ABSTRACT

A packaging element especially useful for surgical sutures is disclosed. The element is formed of a body of pierceable, nonsloughing material such as a closed-cell foam. The element has a recessed needle-receiving region disposed along at least one side edge, including enlarged protective portions disposed at each end of the recessed surface for protecting the suture. The element further includes a central portion configured to receive one or more wraps of ligature material. The package provides protection for the suture, offers versatility in allowing sutures to be positioned on the element in a variety of ways and offers ease of handling, both during the manufacturing process and in use.

5 Claims, 4 Drawing Figures

SUTURE HOLDER

FIELD OF THE INVENTION

This invention relates to packaging sharp objects, such as surgical needles, to which a filamentary material, such as a ligature, is attached.

BACKGROUND OF THE INVENTION

It has become commonplace for suppliers of surgical needles to supply such needles with a length of ligature material secured to the needle. This is especially the case for needles of the relatively smaller sizes, such as those used in opthalmic, neorologic, plastic, vascular and microsurgery. The convention that is adopted in this specification is to refer to the combined unit of the needle and ligature or surgical thread as a "suture". Such sutures can be "single-armed" (i.e., having a needle attached to one end of the ligature) or "double-armed" (i.e., having a needle attached to each end of the ligature).

In order to facilitate use of the suture by the surgeon and prevent the cutting edges or points of the needles from becoming damaged and the ligatures from becoming kinked, knotted or tangled, many different types of packages have been conceived for surgical sutures. In some of these designs, the sharp points of needles are received in a small block of pierceable material and the ligature is either wound about or folded within portions of the package. Examples of such packages are shown in U.S. Pat. Nos. 3,951,261, 3,985,227 and 4,120,395. In these designs, a small block of pierceable material is used to hold the needle and this small piece can become dislodged from its holder and be lost for further use in the surgical field. Also, with packages of this type, the ligatures tend to become tangled.

To overcome these disadvantages, suture packages utilizing a relatively large, flat body of a pierceable, nonsloughing foam material have been proposed and used. In one such package, the holder comprises a somewhat rectangular foam block having two relatively small cut-outs in opposed side edges to receive the needle, the ligature being wrapped about the central portion of the holder. Other forms of suture packages employing blocks of pierceable material to hold and protect sutures are shown in copending application Ser. No. 914,276, filed June 9, 1978 now U.S. Pat. No. 4,183,431.

SUMMARY OF THE INVENTION

It is an object of the invention to provide a packaging element for sutures that provides good protection for the suture, that is convenient and easy to use for the surgeon, that is versatile so that sutures can be packaged on it in a variety of different ways, and that provides ease in mounting the sutures during the packaging operation.

Briefly, these objects are achieved by a packaging element having a recessed surface for receiving the needle extending along a major portion of at least one side edge of the element. The body includes protective portions that extend transversely outwardly of the recessed surface at each end thereof for protecting the suture. In a preferred form, each longitudinal side edge of the element includes such a recessed surface flanked by two transversely extending protective portions of the packaging element. A central longitudinally extending portion of the packaging element comprises a portion about which the surgical thread or ligature of the suture may be wound.

DESCRIPTION OF THE PREFERRED EMBODIMENT

Figure 1:
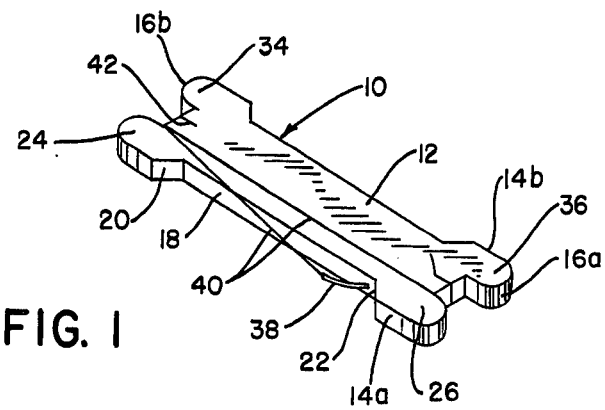
FIG. 1 is an isometric view of a preferred form of packaging element in accordance with the invention and having a suture received thereon.

Referring to FIG. 1, there is shown a suture package 10 that comprises a holder in the form of a shaped body 12 on which is carried a suture comprising a surgical needle 38 to which a surgical thread or ligature 40 is attached. It is desirable that the holder be formed of a material that is pierceable and soft enough to hold a needle without damage to its cutting edges and yet that is of sufficient strength to hold together and not crumble or release debris when a needle is inserted or removed. Also, the material must be of sufficient rigidity so that it remains in a substantially planar condition unless deliberately bent or creased by the user. Preferably, the material is a plastic foam. One found to be particularly suitable is a closed-cell foam sold under the trademark "Volara" by Voltek. This foam is especially preferred because the plastic is foamed by irradiation and therefore the interior portion of the foam is sterilized during its manufacture.

Figure 2:
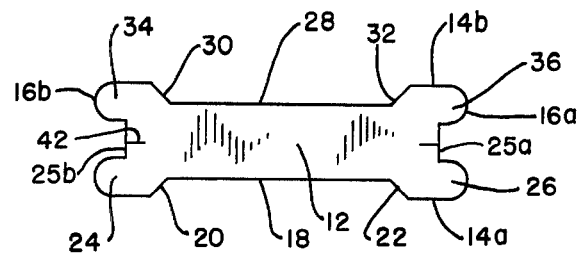
FIG. 2 is a plan view of the packaging element shown in FIG. 1.

As shown in FIGS. 1 and 2, the holder 12, in its preferred form, has an elongated shape having opposed longitudinally extending side surfaces 14a and 14b and opposed transversely extending end surfaces 16a and 16b. The holder 12 is of a thickness so that the point of the needle 38 can be inserted into a surface of the holder and be retained therein and be protected from contact with other portions of the packaging.

Referring again to FIGS. 1 and 2, the holder 12 includes at least one needle-receiving means disposed in one of the side surfaces of the body, such needle-receiving means comprising a recessed surface 18 that is flanked at each end by transversely extending surfaces 20 and 22 that extend from the surface 18 outwardly to the side surface 14a, thereby forming protective enlargements 24 and 26 at each end of the recessed surface 18. These enlargements protect the suture from contact with other portions of the package.

Also, in the preferred shape of holder, each end 16a and 16b includes recessed surfaces 25a and 25b that, together with the central portion of the holder, define a section of the body about which the surgical thread can be wrapped. This central wrapping region may also include suitable means, for example, slits 42, for lightly frictionally retaining an end of the ligature.

It has been found to be especially advantageous if the holder 12 is substantially symmetrical about its longitudinal center line. In this manner, the second longitudinal edge 14b includes a second needle-receiving portion that comprises the recessed surface 28 and transverse surfaces 30 and 32 that extend from the surface 28 to the adjacent side edge 14b, thereby forming two enlarged protective portions 34 and 36.

It should be noted that it is advantageous that the recessed surfaces 18 and 28 extend along a major portion of the longitudinal dimension of the holder 12 and are on the order of one-half or more of that longitudinal dimension. For example, for a holder having a length of about 6.3 cm, measured from surface 16a to surface 16b, it has been found appropriate to have the length of surface 18 or 28 about 3.7 cm.

A very substantial advantage of the holder just described is its versatility. It is adaptable for use with single-armed and double-armed sutures. It is also readily adaptable for use with a wide range of suture lengths, as will become readily apparent.

Figure 4:
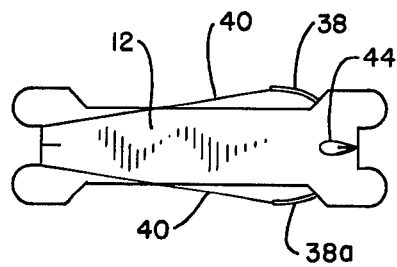
FIG. 4 illustrates another example of how a double-armed suture can be mounted on the packaging element.
Figure 3:
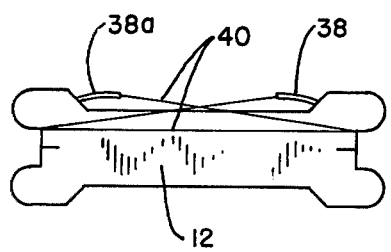
FIG. 3 illustrates one example of how a double-armed suture, or two-single-armed sutures, can be mounted on the packaging element.

Referring to FIG. 3, there is shown one form of suture mounting for a double-armed suture in which one of the needles 38 is placed near one end of the recessed surfaces 28, the ligature wrapped about the central portion of the body in one direction and the other needle 38a positioned near the opposite end of the opposed recess surface 28. It should be understood that a second double-armed suture could be mounted on the opposite recessed surface, thereby providing for the independent mounting of two double-armed sutures on the holder 12. In addition, double-armed sutures can be packaged in the form shown in FIG. 4 in which both needles are positioned at the same end of the holder and the surgical thread 40 is wrapped, in the form of an elongated "V", about the central portion of the holder, the midpoint of the thread forming a loop 44 that is conveniently presented to allow cutting by the surgeon in the event only a single-armed suture is desired.

In addition, relatively short double-armed sutures can be mounted on the holder. For example, a short double-armed suture could be mounted in one of the side recesses of the holder with one of the needles being disposed adjacent the enlargement 24 and with the other needle being disposed adjacent the enlargement 26, with the surgical thread extending between the two needles. A second double-armed suture could be mounted in a similar fashion in the opposite recess. The enlargements 24, 26, 34 and 36 respectively would serve to protect the sutures. Also, one or more relatively short double-armed sutures could be accommodated by inserting the needles at opposed and generally aligned positions in the recesses so that the surgical thread extends across the central portion of the holder in a generally "U"-shaped configuration.

It will readily be seen that the holder 12 having the protective enlargements will reduce the likelihood of abrasion of the suture by contact with other portions of the packaging, for example, covered, thermoformed plastic tubs in which the sutures and holder are stored and shipped in order to maintain sterility prior to use. Further, as previously noted, the holder can receive sutures in a wide variety of ways, thereby allowing a single holder shape to be usable in a substantial number of product packages.

We claim:

1. A suture packaging element comprising a body formed of a substantially planar, pierceable, nonsloughing material, the body having opposed side and end surfaces, a needle-receiving portion formed in a side surface of the body intermediate the opposed ends, the needle receiving portion comprising a recessed surface extending along a major portion of the side surface and a pair of opposed surfaces, one at each end of the recessed surface, extending outwardly from the recessed surface to the adjacent side surface of the body, thereby forming a pair of opposed enlargements, a second needle-receiving portion formed in the side opposite the first-mentioned needle-receiving portion and including a recessed surface extending along a major portion of said opposite side surface and a pair of opposed surfaces, one at each end of the recessed surface and extending outwardly from the recessed surface to the adjacent side surface of the body, thereby forming a second pair of enlargements, one at each end of the body.

2. A packaging element as in claim 1 wherein the enlargements at each end of the body are substantially aligned.

3. A suture packaging element as in claim 1 wherein the body has a longitudinal dimension greater than its transverse dimension and the length of the recessed surface is at least about half the longitudinal length of the body.

4. A suture packaging element as in claim 1 wherein the body is substantially symmetrical about its longitudinal centerline.

5. A suture packaging element as in claim 1, 3 or 4 wherein a surgical needle is disposed in at least one of the portions.

* * * * *